United States Patent [19]

Goldman

[11] 4,258,718

[45] Mar. 31, 1981

[54] MEASURING RESPIRATORY AIR VOLUME

[76] Inventor: Michael D. Goldman, 2700 Southington Rd., Shaker Heights, Ohio 44120

[21] Appl. No.: 30,314

[22] Filed: Apr. 16, 1979

[51] Int. Cl.³ ............................................. A61B 5/08
[52] U.S. Cl. ....................................... 128/653; 128/725
[58] Field of Search ........................... 128/653, 721–729

[56] References Cited

U.S. PATENT DOCUMENTS

| 3,831,586 | 8/1974 | Petit | 128/721 |
| 3,911,899 | 10/1975 | Hattes | 128/653 |
| 4,033,332 | 7/1977 | Hardway et al. | 128/722 |

OTHER PUBLICATIONS

Konno, K. et al., *J. Applied Physiol.*, 22: 407–422 (1967).
Gilbert, R., *Resp. Physiol.* (1971) 13, 238–252.
Gilbert, R., *J. Applied Physiol.* 33: No. 2, Aug. 1972, pp. 252–254.
Spiegel, M., *Statistics*, McGraw-Hill, p. 221 (1961).
Mead, J. et al., *Science* 196: 1383–1384 (1967).
Stagg, D. et al., *J. Applied Physiol.* pp. 623–633, Apr. (1978).

*Primary Examiner*—Kyle L. Howell

[57] ABSTRACT

Apparatus for quantitatively measuring respiratory air volume by summing measurements of the rib cage and abdomen dimensions. During a short calibration interval while the patient breathes normally, the summation coefficients for the rib cage and abdomen measurements are computed from samples of the two measurements taken simultaneously with samples of actual measured respiratory air volume.

15 Claims, 3 Drawing Figures

MEASURING RESPIRATORY AIR VOLUME

FIELD OF THE INVENTION

This invention relates to measuring respiratory air volume in humans or animals.

BACKGROUND OF THE INVENTION

In medical diagnosis and treatment, it is often desirable to quantitatively measure over time the respiratory air volume. This has conventionally been done by having the patient breathe into a mouthpiece connected to a flow rate measuring device. Flow rate is then integrated to give air volume change. But using the mouthpiece has disadvantages. It is difficult to use for long term patient monitoring, especially for ill, sleeping, or anesthetized patients. Furthermore, it is uncomfortable for the patient, tends to restrict breathing, and is generally inconvenient for the physician or technician to use.

There are qualitative respiration monitors available that do not require a mouthpiece, but none provide an accurate measurement of air volume, and are generally used only to signal an attendant when a patient's breathing activity changes sharply or stops. E.g., Petit U.S. Pat. No. 3,831,586, Hardway et al. U.S. Pat. No. 4,033,332, and Hattes U.S. Pat. No. 3,911,899.

Another way of quantitively measuring lung volume is to measure the change in size of the rib cage and abdomen, as it is known that lung volume is a function of these two dimensions. Magnetometers have been used to make the rib cage and abdomen measurements, as disclosed in Mead, Peterson, Grimby, and Mead, "Pulmonary Ventilation Measured From Body Surface Movements," *Science* 196: 1383—1384 (1967). Transmitter coils that generate a magnetic field are secured to the front of the patient's chest and abdomen, and receiver coils that are responsive to changes in the magnetic field are secured to the back (or vice versa). Changes in the magnetic field are the result of changes in the separation between transmitter and receiver, i.e., the diameter of the rib cage and abdomen. Further circuitry produces analog voltages proportional to the diameters.

In using these two measurements to predict changes in lung volume, they must first be calibrated, i.e., coefficients that relate them to respiratory air volume must be determined. To accomplish this calibration, prior magnetometer systems (Kono, K. and J. Mead, "Measurement of the Separate Volume Changes in Rib Cage and Abdomen During Breathing," *J. Applied Physiology* 22: 407–422, 1967) have required that a patient take in a breath through a flow-measuring mouthpiece, and, while holding the breath, shift between two unnatural postures, e.g., an extended abdomen and a retracted abdomen. The patient then breathes in additional air, and again assumes the two postures. Alternatively, the patient could be requested to breathe in two different ways (emphasizing either rib cage or abdominal movements) or in two different postures (e.g., erect or supine). The latter technique is disclosed in Gilbert et al., "Breathing Patterns During $CO_2$ Inhalation Obtained from Motion of the Chest and Abdomen," *Respiration Physiology* 13: 238-252 (1977) and Gilbert et al. "Changes in Tidal Volume, Frequency, and Ventilation Induced by Their Measurement," *Journal of Applied Physiology*, Vol. 33, No. 2, (August 1972). The shift in posture gives two sets of rib cage and abdomen dimensions for the about the same air volume, thereby giving two equations that can be solved for the two unknown coefficients. The unnatural postures required cannot, however, be assumed by many patients, e.g., those who are ill, sleeping, or anesthetized. Furthermore, even when the calibration can be done in this manner, the coefficients obtained are somewhat inaccurate because the air volume is not constant for the two postures due to air compression within the lungs that occurs when the patient assumes the postures. Further error results because of the unnatural spine curvature (i.e., a bending of the trunk) that most patients assume when in the postures.

SUMMARY OF THE INVENTION

It has been discovered that the calibration coefficients for rib-cage and abdomen measurements can be computed directly from data measured during one or more normal breaths, thereby avoiding the above-outlined problems of using artificial postures for calibration and only requiring that a patient breathe through a mouthpiece (or other device for measuring actual respiratory air volume) for several seconds (e.g., 10 seconds). The invention provides an accurate measurement of respiratory air volume without any patient cooperation, thus allowing its use with those patients for whom the prior apparatus was ill suited.

During a normal breath, movement of the rib cage and abdomen are normally out of phase, although in phase at the start and finish of the breath. Thus the ratio of abdomen movement to rib cage movement varies during a breath. It has been found that this variation or phase difference between the two movements can be advantageously used for calibration. During a normal breath, samples are simultaneously taken of the abdomen and rib cage dimensions and of the actual respiratory air volume. These data are then processed to select coefficients that correlate estimated air volume and actual measured air volume.

In preferred embodiments, actual air volume is measured using a mouthpiece to measure respiratory air flow and means are provided for integrating the air flow measurement to give air volume; estimated air volume is determined solely from abdomen and rib-cage dimensions; the two dimensions plus actual measured air volume (derived from a mouthpiece) are sampled for one or more breaths (e.g., 10 seconds or about 3 breaths) with at least 50 samples per breath; the data is stored in the memory of a computer; multi-variable linear regression formulas (e.g., such as those shown in Spiegel, M., *Statistics,* McGraw-Hill, p. 221, 1961) are used to select the coefficients; and means are provided for computing the hysteresis between rib cage and abdomen movement as a signal to the operator of the validity of the calibration.

PREFERRED EMBODIMENT

The structure and operation of a preferred embodiment of the invention will now be described, after first briefly describing the drawings.

DRAWINGS

STRUCTURE

Figure 1:
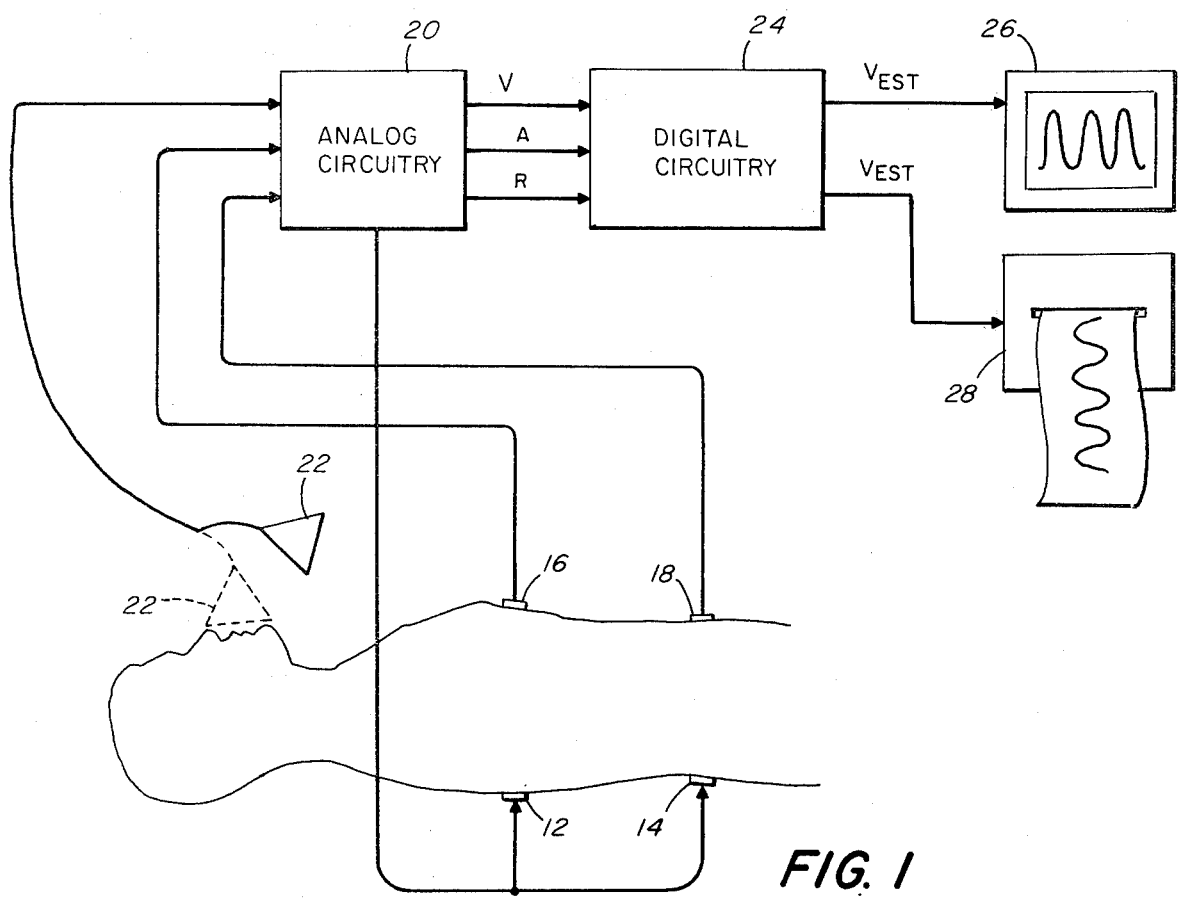
FIG. 1 is a block diagram of the lung volume measuring system.

Referring to FIG. 1, there is shown apparatus for quantitatively measuring respiratory air volume as a function of time. Transmitter magnetometer coils 12, 14 are taped to the back of the patient below the rib cage and abdomen. Corresponding receiver coils 16, 18 are taped to the front surface of the rib cage and abdomen and aligned with the transmitter coils. Analog circuitry 20 drives the transmitter coils, and processes the outputs of the receiver coils to produce analog output signals $X_A$, $X_R$, which are proportional to the diameters of the abdomen and rib cage, respectively. Encased in a round plastic disk, each coil has its winding axis oriented parallel to the skin surface, and is roughly rectangular in shape, being about $\frac{3}{4}$ inch along the axis, and about 7/16 inch by $\frac{3}{8}$ inch across the axis. The coils have inductances of 50 mH.

When calibrating the apparatus, a flow-measuring device 22 is connected to the mouth for a short period. Any one of several types of flow sensors could be used. One type has a roughly one-inch diameter tube inside of which a porous resistance element is mounted. Flow rate is measured by measuring the pressure upstream of the resistance element. Lung or breath volume V is computed by integrating flow rate. The integration is shown being done within block 20, but could as well be accomplished by the digital circuitry of block 24.

Digital circuitry 24 processes the three inputs—lung volume V, abdomen dimension $X_A$, and rib cage dimension $X_R$—to calibrate the apparatus so that respiratory air volume can be accurately estimated from $X_A$ and $X_R$ without continuously measuring flow rate. The calibration computes two coefficients $K_A$ and $K_R$ that relate abdomen and rib cage dimensions to estimated respiratory air volume $V_{EST}$ by the expression $$V_{EST} = K_A X_A + K_R X_R$$

The estimated air volume is displayed either on oscilloscope 26 or strip-chart recorder 28.

Figure 2:
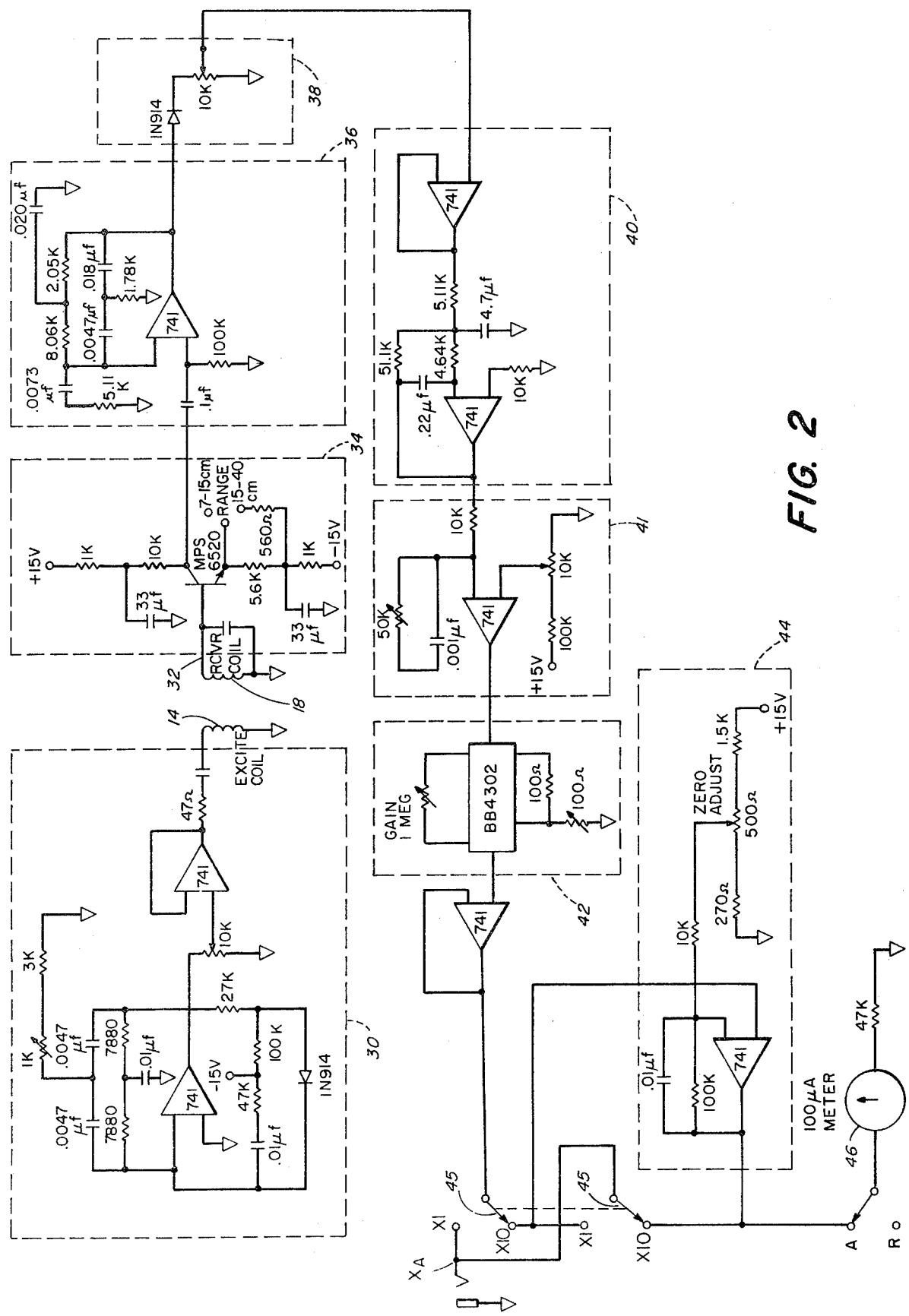
FIG. 2 is a schematic view of the analog circuitry for the magnetometers.

Referring to FIG. 2, there is shown the analog circuitry for the abdomen magnetometer channel. The rib cage channel is identical except that the magnetometer driving frequencies are different to reduce crosstalk between channels. Drive circuitry 30, a buffered balanced-T oscillator, drives transmitter coil 14 at 4300 Hz. (The rib cage transmitter coil is driven at 5900 Hz.) Receiver coil 18 is connected in parallel with a capacitor and the loop is tuned to 4300 Hz to correspond to the transmitter coil. Receiver output 32 is amplified by a single-transistor stage 34 with gain switchable from 2 to 20 to accommodate the differences in coil separation in adults (15 to 40 cm) and children (7 to 15 cm). The amplified output is then fed through bandpass filter 36, which is centered at the coil frequency of 4300 Hz with a gain of 40 and a Q of 20. The filtered signal is then half-wave rectified at 38, and passed through low-pass filter 40 (20 Hz cutoff frequency and gain of 10). The signal is then linearized by a commercially available exponentiator 42, after first being conditioned at block 41 (to assure a non-zero input to the exponentiator). It is then amplified (gain of ten) and zero adjusted at block 44, to produce output $X_A$ for further processing by digital circuitry 24. The analog output can also be displayed at meter 46. Switch 45 is normally in the X10 (gain of ten) position, but can be moved to the X1 (gain of one) position to check linearity of the exponentiator output.

Figure 3:
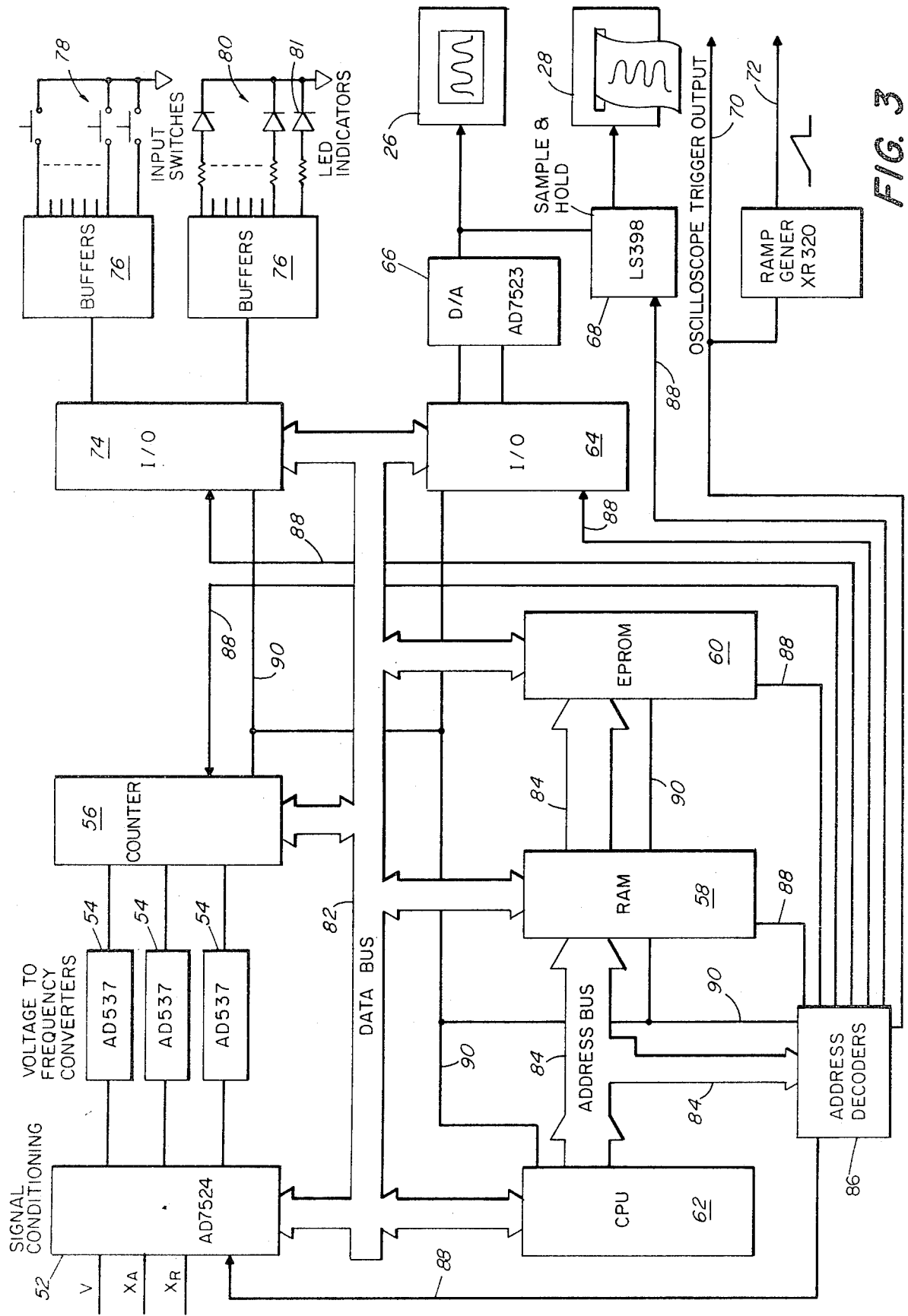
FIG. 3 is a schematic view of the digital circuitry for calibrating the magnetometers and for computing and displaying lung volume.

Referring to FIG. 3, there is shown the digital circuitry for computing the calibration coefficients $K_A$ and $K_R$ and for computing lung volume once the calibration is complete. Analog inputs V, $X_A$, and $X_R$ are converted to digital form by signal conditioning block 52, voltage to frequency converters 54, and frequency counter 56. The digital data are stored in RAM 58 (2K word capacity) in three 256-word buffers, one buffer for each input variable. A program stored in EPROM 60 is used by microprocessor 62 to control the various operations. Data for oscilloscope or strip chart display is processed through input/output chip 64 and digital-to-analog converter 66. Sample and hold circuit 68 is used to slow the analog output down to real time for strip chart display. Trigger output 70 and ramp output 72 are for oscilloscope display purposes. A second input/output chip 74 and buffers 76 provide input switches 78 and corresponding indicator lights 80 for initiation of calibration and for output display selection. An eight bit bidirectional data bus 82 interconnects the various chips, and a 16 bit address bus 84 connects the CPU, RAM, and EPROM. An address decoder 86 activates chip-select lines 88, and a timing-and-control bus 90 is routed to the various devices. Microprocessor 62 can instruct signal conditioning unit 52 to adjust the gains and zero offsets of the input signals to accommodate changes in their amplitude levels.

In both FIGS. 2 and 3, component part numbers are indicated in the various blocks, either by manufacturer's part number or industry standard number. Microprocessor 62, counter 56, and input/output devices 64, 74 are all Z-80 type devices.

OPERATION

In normal operation, after calibration is completed, samples of abdomen and rib cage dimensions $X_A$, $X_R$ are continually taken at 25.6 samples per second, and the new data are stored in the oldest positions of the 256-word buffers, writing over the old data, such that the buffers always contain the most recent 10 seconds of data. As each new sample is taken, the two data points $X_A$, $X_R$ are multiplied by their respective calibration coefficients $K_A$, $K_R$ to compute estimated air volume $V_{EST}$ for that sample. These $V_{EST}$ points are stored in a fourth 256-word buffer. (Measured air volume V is stored in the third buffer for calibration.)

Input switches 78 are used to select one of the stored variables for display on either oscilloscope 26 or recorder 28. All ten seconds of data are displayed in a single oscilloscope sweep, with the horizontal time axis of the oscilloscope being controlled either by trigger signal 70 or by ramp output 72. As new samples are taken, they appear on the oscilloscope trace in place of the old data. About three breaths are displayed over the ten second interval.

To perform a new calibration, flow-measuring device 22 is positioned at the patient's mouth, and samples of measured volume V are taken simultaneously with samples of the abdomen and rib cage dimensions $X_A$, $X_R$. After at least ten seconds, calibration is initiated by activating one of switches 78, thereby temporarily halting data acquisition. For each buffer ($X_A$, $X_R$, V, and $V_{EST}$), the average value of all 256 samples is calculated, and this average is subtracted from each sample point to give a zero mean. This procedure eliminates constant terms, leaving only the coefficients $K_A$ and $K_R$ to be computed. Conventional two-variable linear regression formulas are then implemented by the program stored in EPROM 60. The regression procedure gives the coefficients that maximize the correlation between measured volume V and estimated volume $V_{EST}$.

As a warning to the operator that the calibration may be erroneous, a measure of the hysteresis between rib cage and abdomen movements is also computed during the calibration. The hysteresis is the amount of area inside a curve of the abdomen dimension $X_A$ plotted versus the rib cage dimension $X_R$. Normally, there is significant hysteresis because the rib cage and abdomen movements are out of phase with each other during a breath. Indeed, it is the presence of the hysteresis that provides adequate data for computing the coefficients. In some circumstances, however, a patient may breathe in such a manner that the abdomen and rib-cage movements are nearly in phase. If this is the manner that the patient always breathes, the calibration is as good as any other. In some cases, however, the patient may resume breathing with out-of-phase movements after the calibration. In this situation, the calibration must be repeated. Indicator light 81 is turned on if hysteresis is low.

Although not shown in FIG. 3, the digital circuitry also displays the calculated coefficients $K_A$, $K_R$; computes and displays the respiratory rate, average breath volume (i.e., tidal volume), and total, one-minute respiratory volume ("minute ventilation"); and initiates alarms based on exceeding limits on these parameters (for patient monitoring).

OTHER EMBODIMENTS

Other embodiments of the invention are within the following claims. For example, other abdomen and rib cage sensors (e.g., mechanical or electronic) could replace the magnetometers; a small magnetometer coil (e.g., 1/16 by ¼ inch with an inductance of 1 mH and driven at 16 KHz) could be used for infants; larger currents could increase the useful range of the described magnetometers to the dimensions (e.g., 28 inches) required for large animals; a volume measuring device could be substituted for the air-flow measuring device shown during calibration; and additional measurements of abdomen and rib cage dimensions could be made, thereby increasing the number of coefficients to be computed by the calibration procedure. Furthermore, the coefficients could be computed in ways other than shown, e.g., by using an analog computer or by following an iterative procedure (e.g., as in Stagg, D., M. Goldman, and J. Newsom Davis "Computer Aided Measurement of Breath Volume and Time Components Using Magnetometers," J. Applied Physiology, pp. 623–633, April, 1978, hereby incorporated by reference) that would not require storing data for the whole calibration interval.

What is claimed is:

1. Apparatus for measuring respiratory air volume, comprising:
   means for determining an estimate of respiratory air volume, comprising
      an abdomen sensor for measuring an abdomen dimension,
      a rib-cage sensor for measuring a rib-cage dimension,
      means for determining the sum of said abdomen dimension multiplied by an abdomen coefficient plus said rib-cage dimension multiplied by a rib-cage coefficient, and
      means for providing an estimated respiratory air volume output, and
   means for calibrating while the patient breathes normally, comprising
      means for measuring actual respiratory air volume,
      means for simultaneously sampling said abdomen dimension, said rib-cage dimension, and said actual air volume at a plurality of times during each breath of a calibration interval, said interval extending for one or more normal breaths, said sampling occurring frequently enough to generate during a single said breath a multiplicity of sets of data representing said dimensions and said volume, with the relative contributions of rib-cage and abdominal displacements varying from set to set despite the absence of respiratory maneuver other than normal breathing, and
      means for processing said samples to select values for said abdomen and rib-cage coefficients that correlate said estimated air volume and said actual air volume.

2. The apparatus of claim 1 wherein
   said means for calibrating further comprises means for storing said samples during said calibration interval and
   means for processing includes means for performing multi-variable linear regression analysis on said stored samples to compute said coefficients.

3. The apparatus of claim 1 wherein said means and determining comprises means for estimating respirator air volume solely on the basis of said sum.

4. The apparatus of claim 1 wherein said means for simultaneous sampling comprises means for simultaneous sampling over a calibration interval extending for a plurality of breaths.

5. The apparatus of claim 1 wherein said means for simultaneous sampling comprises means for taking at least 50 samples per breath.

6. The apparatus of claim 1 wherein said means for simultaneous sampling comprises means for taking at least 15 samples per second.

7. The apparatus of claim 1 further comprising means for displaying said estimated air volume.

8. The apparatus of claim 1 further comprising means for determining when hysteresis between said abdomen and rib-cage dimensions is abnormally low during said calibration interval, said means including means for giving an indication that hysteresis is abnormally low, thereby alerting the operator that the calibration may be erroneous.

9. The apparatus of claim 1 wherein said means for measuring actual respiratory air volume includes a mouthpiece for measuring respiratory air flow.

10. A method for measuring respiratory air volume, comprising the steps of:
   determining an estimate of respiratory air volume by measuring a dimension of the abdomen with an abdomen sensor,
   measuring a dimension of the rib-cage with a rib-cage sensor, and
   determining an estimated respiratory air volume output,
      determining the sum of said abdomen dimension multiplied by an abdomen coefficient plus said rib-cage dimension multiplied by a rib-cage coefficient, and performing a calibration while the patient breathes normally to determine said abdomen and rib-cage coefficients by measuring actual respiratory air volume, simultaneously sampling said abdomen dimensions, said rib-cage dimension, and said actual air volume at a plurality of times during each breath of a calibration interval, said interval extending for one or more normal breaths, said sampling occurring forequently enough to generate during a single said breath a multiplicity of sets of data representing said dimensions and said volume, with the relative contributions of rib-cage and abdominal displacements varying from set to set despite the absence of respiratory maneuver other than normal breathing, and processing said samples to select said abdomen and rib-cage coefficients that correlate said estimated air volume and said actual air volume.

11. The method of claim 10 including the steps of storing said samples during said calibration interval and performing multi-variable linear regression analysis on said stored samples to compute said coefficients.

12. The method of claim 10 wherein there are at least 50 samples taken during each breath.

13. The method of claim 10 further comprising the step of determining the hysteresis between said abdomen and rib-cage dimensions during said calibration interval, whereby when hysteresis is abnormally low an indication can be given the operator that the calibration may be erroneous.

14. The apparatus of claim 1 wherein said abdomen and rib-cage dimensions are cross-sectional dimensions.

15. The apparatus of claim 14 wherein said abdomen and rib-cage sensors comprise magnetometers.

* * * * *